United States Patent

Gayer et al.

[11] Patent Number: 5,728,729
[45] Date of Patent: Mar. 17, 1998

[54] 3-METHOXY-2-PHENYLACRYLIC ACID ESTERS USED AS PEST-CONTROL AGENTS, ESPECIALLY AS FUNGICIDES

[75] Inventors: Herbert Gayer, Monheim; Peter Gerdes, Aachen; Heinz-Wilhelm Dehne, Bonn, all of Germany

[73] Assignee: Bayer Aktiengesellschaft, Leverkusen, Germany

[21] Appl. No.: 553,360

[22] PCT Filed: May 4, 1994

[86] PCT No.: PCT/EP94/01417

§ 371 Date: Nov. 13, 1995

§ 102(e) Date: Nov. 13, 1995

[87] PCT Pub. No.: WO94/26705

PCT Pub. Date: Nov. 24, 1994

[30] Foreign Application Priority Data

May 17, 1993 [DE] Germany .............. 43 16 431.5

[51] Int. Cl.[6] .................. A01N 47/22; C07C 333/10
[52] U.S. Cl. .................. 514/487; 514/478; 514/484; 514/486; 514/490; 558/233
[58] Field of Search ............ 558/233; 514/484, 514/486, 487, 490

[56] References Cited

FOREIGN PATENT DOCUMENTS

93/07116  4/1993  WIPO.

OTHER PUBLICATIONS

Makhsumov, A.G. et al. Chemical Abstracts. vol. 88(Jun. 1978): Abstract No. 190561.

*Primary Examiner*—Michael G. Ambrose
*Attorney, Agent, or Firm*—Sprung Kramer Schaefer & Briscoe

[57] ABSTRACT

3-Methoxy-2-phenyl-acrylic esters of the formula

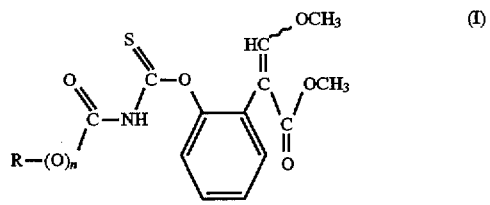

in which
R represents optionally substituted alkyl, cycloalkyl or aryl and
n represents a number 0 or 1,
a process for their preparation and their use as pesticides.

8 Claims, No Drawings

3-METHOXY-2-PHENYLACRYLIC ACID ESTERS USED AS PEST-CONTROL AGENTS, ESPECIALLY AS FUNGICIDES

This application was filed under 35 USC 371 and was based upon PCT International Application No. PCT/EP94/01417, filed May 4, 1994.

The invention relates to new 3-methoxy-2-phenyl-acrylic esters, to a process for their preparation, and to their use as pesticides.

It has already been disclosed that certain 3-methoxy-2-phenyl-acrylic esters have fungicidal properties (cf. EP-OS (European Published Specification) 0 178 826). For example, methyl 3-methoxy-2-(2-benzoyloxyphenyl)-acrylate can be used for combating fungi. However, the activity of this substance is not entirely satisfactory in all fields of application when used at low rates.

There have now been found new 3-methoxy-2-phenyl-acrylic esters of the formula

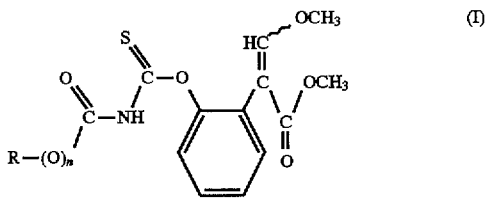

in which
R represents in each case optionally substituted alkyl, cycloalkyl or aryl and
n represents a number 0 or 1,
with the exception of methyl 2-[N-(3,5-benzoyl)-thiocarbamoyloxy]-phenyl-3-methoxyacrylate.

If appropriate, the compounds of the formula (I) can exist as geometric and/or optical isomers or variously composed isomer mixtures, depending on the nature of the substituents. The invention relates to the pure isomers and to the isomer mixtures.

Furthermore, it has been found that 3-methoxy-2-phenyl-acrylic esters of the formula (I) are obtained when methyl 2-(2-hydroxyphenyl)-3-methoxy-acrylate, of the formula

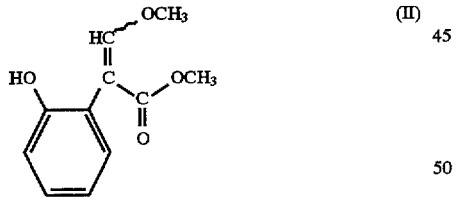

is reacted with N-acyl-isothiocyanates of the formula

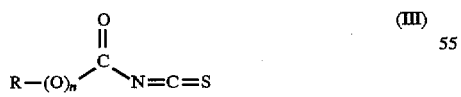

in which
R and n have the abovementioned meaning,
if appropriate in the presence of a diluent and if appropriate in the presence of an acid-binding agent.

Finally, it has been found that the new 3-methoxy-2-phenyl-acrylic esters of the formula (I) are highly suitable for use as pesticides.

Surprisingly, the 3-methoxy-2-phenyl-acrylic esters of the formula (I) according to the invention show a considerably better activity against phytopathogenic microorganisms than, for example, methyl 3-methoxy-2-(2-benzoyloxyphenyl)-acrylate, which is a prior-art active compound of the same direction of action and a similar constitution.

Formula (I) provides a general definition of the 3-methoxy-2-phenyl-acrylic esters according to the invention.

R preferably represents straight-chain or branched alkyl having 1 to 8 carbon atoms, cycloalkyl having 3 to 8 carbon atoms, or aralkyl or aryl, each of which has 6 to 10 carbon atoms in the aryl moiety and, if appropriate, 1 to 6 carbon atoms in the straight-chain or branched alkyl moiety and each of which is optionally monosubstituted to pentasubstituted by identical or different substituents, it being possible for the aryl moiety in each case to be substituted by halogen, cyano, nitro, formyl, carbamoyl, thiocarbamoyl, in each case straight-chain or branched alkyl, alkoxy, alkylthio, alkylsulphinyl or alkylsulphonyl, each of which has 1 to 6 carbon atoms, in each case straight-chain or branched alkenyl or alkenyloxy, each of which has 2 to 6 carbon atoms, in each case straight-chain or branched halogenoalkyl, halogenoalkoxy, halogenoalkylthio, halogenoalkylsulphinyl or halogenoalkylsulphonyl, each of which has 1 to 6 carbon atoms and 1 to 13 identical or different halogen atoms, in each case straight-chain or branched halogenoalkenyl or halogenoalkenyloxy, each of which has 2 to 6 carbon atoms and 1 to 13 identical or different halogen atoms, in each case straight-chain or branched N-alkylamino, dialkylamino, alkylcarbonyl, alkylcarbonyloxy, alkoxycarbonyl, alkylsulphonyloxy, hydroximinoalkyl or alkoximinoalkyl, each of which has 1 to 6 carbon atoms in the individual alkyl or alkoxy moieties, in each case divalent alkylene or dioxyalkylene, each of which has 1 to 6 carbon atoms and each of which is optionally monosubstituted to pentasubstituted by identical or different substituents from the series consisting of halogen, straight-chain or branched alkyl having 1 to 4 carbon atoms and straight-chain or branched halogenoalkyl having 1 to 4 carbon atoms and 1 to 9 identical or different halogen atoms, cycloalkyl having 3 to 7 carbon atoms, 3 to 7-membered heterocyclyl having 2 to 6 carbon atoms and 1 to 3 identical or different hetero atoms—in particular nitrogen, oxygen and/or sulphur-, and phenyl, phenoxy, benzyl, benzyloxy, phenylethyl and/or phenylethyloxy, each of which is optionally monosubstituted to pentasubstituted in the phenyl moiety by identical or different substituents from the series consisting of halogen, straight-chain or branched alkyl having 1 to 4 carbon atoms, straight-chain or branched halogenoalkyl having 1 to 4 carbon atoms and 1 to 9 identical or different halogen atoms, straight-chain or branched alkoxy having 1 to 4 carbon atoms and straight-chain or branched halogenoalkoxy having 1 to 4 carbon atoms and 1 to 9 identical or different halogen atoms.

n also preferably represents a number 0 or 1.

R particularly preferably represents straight-chain or branched alkyl having 1 to 6 carbon atoms, cycloalkyl having 3 to 7 carbon atoms, or aralkyl or aryl, each of which has 6 or 10 carbon atoms in the aryl moiety and, if appropriate, 1 to 4 carbon atoms in the straight-chain or branched alkyl moiety and each of which is optionally monosubstituted to pentasubstituted by identical or different substituents, it being possible for the aryl moiety in each case to be substituted by halogen, cyano, nitro, formyl, carbamoyl, thiocarbamoyl, in each case straight-chain or branched alkyl, alkoxy, alkylthio, alkylsulphinyl or alkylsulphonyl, each of which has 1 to 4 carbon atoms, in each case straight-chain or branched alkenyl or alkenyloxy, each of which has 2 to 4 carbon atoms, in each case straight-chain or branched halogenoalkyl, halogenoalkoxy, halogenoalkylthio, halogenoalkylsulphinyl or halogenoalkylsulphonyl, each of which has 1 to 4 carbon atoms and 1 to 9 identical or different halogen atoms, in each case straight-chain or branched halogenoalkenyl or halogenoalkenyloxy, each of which has 2 to 4 carbon atoms and 1 to 9 identical or different halogen atoms, in each case straight-chain or branched N-alkylamino, dialkylamino, alkylcarbonyl, alkylcarbonyloxy, alkoxycarbonyl, alkylsulphonyloxy, hydroximinoalkyl or alkoximinoalkyl, each of which has 1 to 4 carbon atoms in the individual alkyl or alkoxy moieties, in each case divalent alkylene or dioxyalkylene, each of which has 1 to 4 carbon atoms and each of which is optionally monosubstituted to pentasubstituted by identical or different substituents from the series consisting of halogen, straight-chain or branched alkyl having 1 to 3 carbon atoms and straight-chain or branched halogenoalkyl having to 1 to 3 carbon atoms and 1 to 7 identical or different halogen atoms, cycloalkyl having 3 to 6 carbon atoms, 5- to 7-membered saturated heterocyclyl having 4 to 6 carbon atoms and 1 or 2 identical or different hetero atoms—in particular nitrogen, oxygen and/or sulphur-, and phenyl, phenoxy, benzyl, benzyloxy, phenylethyl and/or phenylethyloxy, each of which is optionally monosubstituted to trisubstituted in the phenyl moiety by identical or different substituents from the series consisting of halogen, straight-chain or branched alkyl having 1 to 3 carbon atoms, straight-chain or branched halogenoalkyl having 1 to 3 carbon atoms and 1 to 7 identical or different halogen atoms, straight-chain or branched alkoxy having 1 to 3 carbon atoms and straight-chain or branched halogenoalkoxy having 1 to 3 carbon atoms and 1 to 7 identical or different halogen atoms.

n also particularly preferably represents a number 0 or 1.

R very particularly preferably represents straight-chain or branched alkyl having 1 to 4 carbon atoms, or represents cyclopropyl, cyclopentyl or cyclohexyl, or represents phenyl, naphthyl, benzyl or naphthylmethyl, each of which is optionally monosubstituted to trisubstituted by identical or different substituents, it being possible for the aryl moiety to be substituted in each case by fluorine, chlorine, bromine, cyano, nitro, formyl, carbamoyl, thiocarbamoyl, methyl, ethyl, n- or i-propyl, n-, i-, s- or t-butyl, methoxy, ethoxy, n- or i-propoxy, n-, i-, s- or t-butoxy, methylthio, ethylthio, methylsulphinyl, methylsulphonyl, allyl, butenyl, allyloxy, butenyloxy, trifluoromethyl, trifluoromethoxy, difluoromethoxy, trifluoromethylthio, difluorochloromethylthio, trifluoromethylsulphinyl, trifluoromethylsulphonyl, dimethylamino, diethylamino, acetyl, acetoxy, methylsulphonyloxy, ethylsulphonyloxy, methoxycarbonyl, ethoxycarbonyl, hydroximinomethyl, hydroximinoethyl, methoximinomethyl, methoximinoethyl, ethhoximinomethyl, ethoximinoethyl, propane-1,3-diyl, butane-1,4-diyl, dioxymethylene, dioxyethylene, dioxypropylene, difluorodioxymethylene, trifluorodioxyethylene, trifluorochlorodioxyethylene, tetrafluorodioxyethylene, cyclopropyl, cyclopentyl, cyclohexyl, 1-pyrrolidinyl, 1-piperidinyl, 1-perhydroazepinyl, 4-morpholinyl and/or phenyl, phenoxy, benzyl or benzyloxy, each of which is optionally monosubstituted to trisubstituted by identical or different substituents from the series consisting of fluorine, chlorine, bromine, methyl, ethyl, methoxy, ethoxy, trifluoromethyl and/or trifluoromethoxy.

n also very particularly preferably represents the number 0 or 1.

In addition to the compounds mentioned in the preparation examples, the following 3-methoxy-2-phenyl-acrylic esters of the formula (I) my be mentioned individually:

TABLE 1

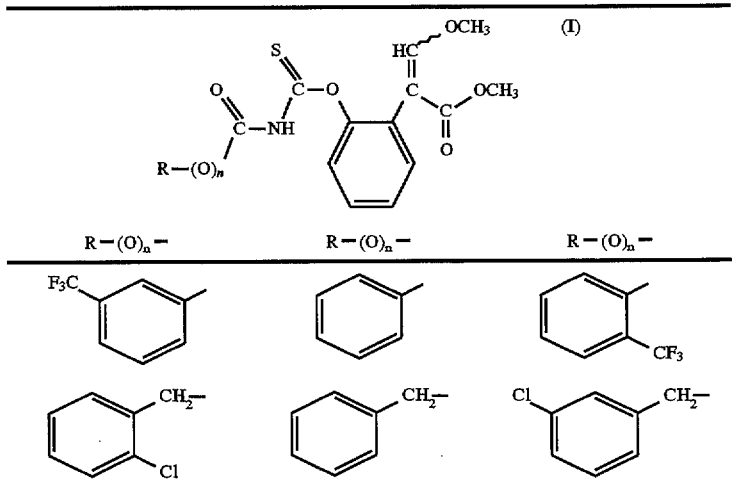

TABLE 1-continued

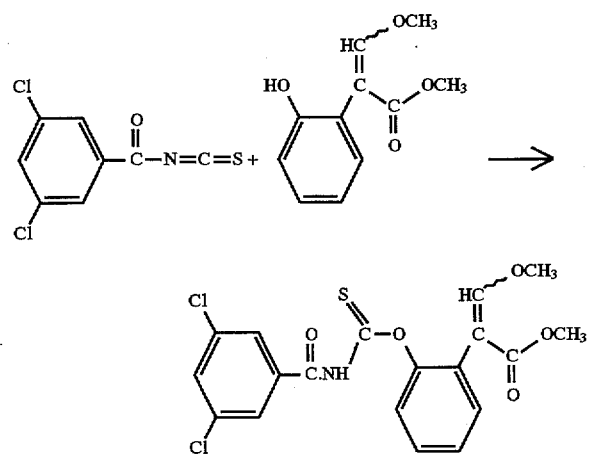

If, for example, methyl 2-(2-hydroxyphenyl)-3-methoxy-acrylate and 3,5-dichlorobenzoyl isothiocyanate are used as starting substances, the come of the reaction of the process according to the invention can be represented by the following equation:

Methyl 2-(2-hydroxyphenyl)-3-methoxy-acrylate, of the formula (II), which is required as starting compound for carrying out the process according to the invention, has been disclosed (cf. EP-OS (European Published Specification) 0 242 081).

Formula (III) provides a general definition of the N-acyl-isothiocyanates which are furthermore required as starting substances for carrying out the process according to the invention. In this formula, R and n preferably represent those radicals and indices which have already been mentioned in connection with the description of the compounds of the formula (I) according to the invention as being preferred for this substituent and this index.

The N-acyl-isothiocyanates of the formula (III) are generally known compounds of organic chemistry (cf. Houben-Weyl "Methoden der Organischen Chemie" (Methods of Organic Chemistry), Volume 9, p. 878, Thieme Verlag, Stuttgart, J. Am. Chem. Soc. 56, 719, 1408 [1934]; and Organic Syntheses 28, 89 [1948]).

Diluents which are suitable for carrying out the process according to the invention are inert organic solvents. The following can preferably be used: aliphatic, alicyclic or aromatic, optionally halogenated hydrocarbons, such as, for example, benzine, benzene, toluene, xylene, chlorobenzene, dichlorobenzene, petroleum ether, hexane, cyclohexane, dichloromethane, chloroform, carbon tetrachloride; ethers, such as diethyl ether, diisopropyl ether, dioxane, tetrahydrofuran or ethylene glycol dimethyl ether or ethylene glycol diethyl ether; nitriles, such as acetonitrile, propionitrile or benzonitrile; amides, such as N,N-dimethylformamide, N,N-dimethylacetamide, N-methylformanilide, N-methylpyrrolidone or hexamethylphosphoric triamide, or sulphoxides, such as dimethyl sulphoxide.

When carrying out the process according to the invention, suitable acid-binding agents are all customary inorganic or organic bases. The following can preferably be used: the hydrides, hydroxides, amides, alcoholates, acetates, carbonates or hydrogen carbonates of alkaline earth metals or alkali metals, or ammonium compounds, such as, for example, sodium hydride, sodium amide, sodium methylate, sodium ethylate, potassium tert-butylate, sodium hydroxide, potassium hydroxide, ammonium hydroxide, sodium acetate, potassium acetate, calcium acetate, ammonium acetate, sodium carbonate, potassium carbonate, potassium hydrogen carbonate, sodium hydrogen carbonate or ammonium carbonate, and also tertiary amines, such as trimethylamine, triethylamine, tributylamine, N,N-dimethylaniline, pyridine, N-methylpiperidine, N,N-dimethylaminopyridine, diazabicyclooctane (DABCO), diazabicyclononene (DBN) or diazabicycloundecene (DBU).

When carrying out the process according to the invention, the reaction temperatures can be varied within a substantial range. In general, the process is carried out at temperatures between −30° C. and +100° C., preferably at temperatures between −20° C. and +60° C.

The process according to the invention is conventionally carried out under atmospheric pressure. However, it is also possible to carry out the process under elevated or reduced pressure.

To carry out the process according to the invention, 1.0 to 3.0 mol, preferably 1.0 to 1.5 mol, of N-acyl-isothiocyanate of formula (III) and, if appropriate, 0.01 to 1.0 mol, preferably 0.1 to 0.5 mol, of acid-binding agent are generally employed per mole of methyl 2-(2-hydroxyphenyl)-3-methoxy-acrylate, of the formula (II). The reaction is carried out and the reaction products are worked up and isolated by known processes (cf. in this context also the preparation examples).

The end products of the formula (I) are purified with the aid of customary processes, for example by column chromatography or by recrystallization.

They are characterized with the aid of the melting point or, in the case of compounds which do not crystallize, with the aid of the refractive index or of proton nuclear resonance spectroscopy ($^1$H NMR).

The active compounds according to the invention have a powerful action against pests and can be employed in practice for combating undesirable microorganisms. The active compounds are suitable for use as plant protection agents, in particular as fungicides.

Fungicidal agents in plant protection are employed for combating Plasmodiophoromycetes, Oomycetes, Chytridiomycetes, Zygomycetes, Ascomycetes, Basidiomycetes and Deuteromycetes.

Some causative organisms of fungal diseases which come under the generic names listed above may be mentioned as examples, but not by way of limitation:

Pythium species, such as, for example, *Pythium ultimum*;

Phytophthora species, such as, for example, *Phytophthora infestans*;

Pseudoperonospora species, such as, for example, *Pseudoperonospora humuli* or *Pseudoperonospora cubensis*;

Plasmopara species, such as, for example, *Plasmopara viticola*;

Peronospora species, such as, for example, *Peronospora pisi* or *Peronospora brassicae*;

Erysiphe species, such as, for example, *Erysiphe graminis*;

Sphaerotheca species, such as, for example, *Sphaerotheca fuliginea*;

Podosphaera species, such as, for example, *Podosphaera leucotricha*;

Venturia species, such as, for example, *Venturia inaequalis*;

Pyrenophora species, such as, for example, *Pyrenophora teres* or *Pyrenophora graminea* (conidia form: Drechslera, synonym: Helminthosporium);

Cochliobolus species, such as, for example, *Cochliobolus sativus* (conidia form: Drechslera, synonym: Helminthosporium);

Uromyces species, such as, for example, *Uromyces appendiculatus*;

Puccinia species, such as, for example, *Puccinia recondita*;

Tilletia species, such as, for example, *Tilletia caries*;

Ustilago species, such as, for example, *Ustilago nuda* or *Ustilago avenae*;

Pellicularia species, such as, for example, *Pellicularia sasakii*;

Pyricularia species, such as, for example, *Pyricularia oryzae*;

Fusarium species, such as, for example, *Fusarium culmorum*;

Botrytis species, such as, for example, *Botrytis cinerea*;

Septoria species, such as, for example, *Septoria nodorum*;

Leptosphaeria species, such as, for example, *Leptosphaeria nodorum*;

Cercospora species, such as, for example, *Cercospora canescens*;

Alternaria species, such as, for example, *Alternaria brassicae* and

Pseudocercosporella species, such as, for example, *Pseudocercosporella herpotrichoides*.

The good toleration, by plants, of the active compounds, at the concentrations required for combating plant diseases, permits treatment of above-ground parts of plants, of vegetative propagation stock and seeds, and of the soil.

The active compounds according to the invention can be employed particularly successfully for combating diseases in fruit and vegetable growing, such as, for example, against the causative organism of apple scab (*Venturia inaequalis*), or for combating cereal diseases, such as, for example, against the causative organism of powdery mildew of cereals (*Erysiphe graminis*) or against the causative organism of glume blotch of wheat (*Septoria nodorum*) or against the causative organism of net blotch of barley (*Pyrenophora teres*), or for combating rice diseases, such as, for example, against the causative organism of rice blast disease (*Pyricularia oryzae*). In addition, the active compounds according to the invention have a good in vitro activity.

Moreover, the active compounds according to the invention also have a leaf-acting insecticidal action.

Depending on their particular physical and/or chemical properties, the active compounds can be converted to the customary formulations, such as solutions, emulsions, suspensions, powders, foams, pastes, granules, aerosols, very free capsules in polymeric substances and in coating composition for seed, as well as ULV cold mist and warm mist formulations.

These formulations are produced in a known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water; by liquefied gaseous extenders or carriers are meant liquids which are gaseous at ambient temperature and under atmospheric pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly-disperse silica, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumen hydrolysis products; as dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention, as such or in their formulations can preferably be used as a mixture with known fungicides, bactericides, acaricides, nematicides or insecticides. This is to widen the spectrum of action or to prevent the build-up of resistance. In many cases, synergistic effects are observed.

Examples of suitable components for mixtures are the following substances.

Fungicides 2-aminobutane; 2-anilino-4-methyl-6-cyclopropyl-pyrimidine; 2',6'-dibromo-2-methyl-4'-trifluoromethoxy-4'-trifluoro-methyl-1,3-thizole-5-carboxanilide; 2,6-dichloro-N-(4-trifluoromethylbenzyl)benzamide; (E)-2-methoxyimino-N-methyl-2-(2-phenoxyphenyl) acetamide; 8-hydroxyquinoline sulphate; methyl (E)-2-{2-[6-(2-cyanophenoxy)pyrimidin-4-yloxy]phenyl}-3-methoxyacrylate; methyl (E)-methoximino[alpha-(o-tolyloxy)-o-tolyl]acetate; 2-phenylphenol (OPP), aldimorph, ampropylfos, anilazine, azaconazole, benalaxyl, benodanil, benomyl, binapacryl, biphenyl, bitertanol, blasticidin-S, bromuconazole, bupirimate, buthiobate, calcium polysulphide, captafol, captan, carbendazim, carboxin, quinomethionate, chloroneb, chloropicrin, chlorothalonil, chlozolinate, cufraneb, cymoxanil, cyproconazole, cyprofuran, dichlorophen, diclobutrazol, diclofluanid, diclomezin, dicloran, diethofencarb, difenoconazole, dimethirimol, dimethomorph, diniconazole, dinocap, diphenylamine, dipyrithion, ditalimfos, dithianon, dodine, drazoxolon, edifenphos, epoxyconazole, ethirimol, etridiazole, fenarimol, fenbuconazole, fenfuram, fenitropan, fenpiclonil, fenpropidin, fenpropimorph, fentin acetate, fentin hydroxide, ferbam, fefimzone, fluazinam, fludioxonil, fluoromide, fluquinconazole, flusilazole, flusulfamide, flutolanil, flutriafol, folpet, fosetyl-aluminium, fthalide, fuberidazole, furalaxyl, furmecyclox, guazatine, hexachlorobenzene, hexaconazole, hymexazol, imazalil, imibenconazole, iminoctadine, iprobenfos (IBP), iprodione, isoprothiolane, kasugamycin, copper preparations such as: copper hydroxide, copper naphthenate, copper oxychloride, copper sulphate, copper oxide, oxine-copper and Bordeaux mixture, mancopper, mancozeb, maneb, mepanipyrim, mepronil, metalaxyl, metconazole, methasulfocarb, methfuroxam, metiram, metsulfovax, myclobutanil, nickel dimethyldithiocarbamate, nitrothal-isopropyl, nuarimol, ofurace, oxadixyl, oxamocarb, oxycarboxin, pefurazoate, penconazole, pencycuron, phosdiphen, pimaricin, piperalin, polyoxin, probenazole, prochloraz, procymidone, propamocarb, propiconazole, propineb, pyrazophos, pyrifenox, pyrimethanil, pyroquilon, quintozene (PCNB), sulphur and sulphur preparations, tebuconazole, tecloftalam, tecnazene, tetraconazole, thiabendazole, thicyofen, thiophanate-methyl, thiram, tolclophos-methyl, tolylfluanid, triadimefon, triadimenol, triazoxide, trichlamide, tricyclazole, tridemorph, triflumizole, triforine, triticonazole, validamycin A, vinclozolin, zineb, ziram.

Bactericides bronopol, dichlorophen, nitrapyrin, nickel dimethyldithiocarbamate, kasugamycin, octhilinone, furanecarboxylic acid, oxytetracyclin, probenazole, streptomycin, tecloftalam, copper sulphate and other copper preparations.

Insecticides/Acaricides/Nematicides abamectin, abamectin, AC 303 630, acephate, acrinathrin, alanycarb, aldicarb, alphamethrin, amitraz, avermectin, AZ 60541, azadirachtin, azinphos A, azinphos M, azocyclotin, Bacillus thuringiensis, bendiocarb, benfuracarb, bensultap, betacyluthrin, bifenthrin, BPMC, brofenprox, bromophos A, bufencarb, buprofezin, butocarboxin, butylpyridaben, cadusafos, carbaryl, carbofuran, carbophenothion, carbosulfan, cartap, CGA 157 419, CGA 184699, chloethocarb, chlorethoxyfos, chloretoxyfos, chlorfenvinphos, chlorfluazuron, chlormephos, chlorpyrifos, chlorpyrifos M, cis-resmethrin, clocythrin, clofentezine, cyanophos, cycloprothrin, cyfluthrin, cyhalothrin, cyhexatin, cypermethrin, cyromazine, deltamethrin, demeton M, demeton S, demeton-S-methyl, diafenthiuron, diazinon, dichlofenthion, dichlorvos, dicliphos, dicrotophos, diethion, diflubenzuron, dimethoate, dimethylvinphos, dioxathion, disulfoton, edifenphos, emamectin, esfenvalerate, ethiofencarb, ethion, ethofenprox, ethoprophos, etofenprox, etrimphos, fenamiphos, fenazaquin, fenbutatin oxide, fenitrothion, fenobucarb, fenothiocarb, fenoxycarb, fenpropathrin, fenpyrad, fenpyroximate, fenthion, fenvalerate, fipronil, fluazinam, flucycloxuron, flucythrinate, flufenoxuron, flufenprox, fluvalinate, fonophos, formothion, fosthiazate, fubfenprox, furathiocarb, HCH, heptenophos, hexaflumuron, hexythiazox, imidacloprid, iprobenfos, isazophos, isofenphos, isoprocarb, isoxathion, ivemectin, lamda-cyhalothrin, lufenuron, malathion, mecarbam, mervinphos, mesulfenphos, metaldehyde, methacrifos, methamidophos, methidathion, methiocarb, methomyl, metolcarb, milbemectin, monocrotophos, moxidectin, naled, NC 184, NI 25, nitenpyram omethoate, oxamyl, oxydemethon M, oxydeprofos, parathion A, parathion M, permethrin, phenthoate, phorate, phosalone, phosmet, phosphamdon, phoxirn, pirimicarb, pirimiphos M, pirimiphos A, profenofos, profenophos, promecarb, propaphos, propoxur, prothiofos, prothiophos, prothoate, pymetrozin, pyrachlophos, pyraclofos, pyrachlophos, pyradaphenthion, pyresmethrin, pyrethrum, pyridaben, pyrimidifen, pyriproxifen, quinalphos, RH 5992, salithion, sebufos, silafluofen, sulfotep, sulprofos, tebufenozid, tebufenpyrad, tebupirimiphos, teflubenzuron, tefluthrin, temephos, terbam, terbufos, tetrachlorvinphos, thiafenox, thiodicarb, thiofanox, thiomethon, thionazin, thuringiensin, tralomethrin, triarathen, triazophos, triazuron, trichlorfon, triflumuron, trimethacarb, vamidothion, XMC, xylylcarb, YI 5301/5302, zetamethrin.

A mixture with other known compounds, such as herbicides, or with fertilizers and growth regulators, is also possible.

The active compounds can be used as such, in the form of their formulations or in the use forms prepared therefrom, such as ready-to-use solution, suspensions, wettable powders, pastes, soluble powders, dusts and granules. They are used in the customary manner, for example by watering, spraying atomizing, scattering, dusting, foaming, brushing on and the like. It is furthermore possible to apply the active compounds by the ultra-low-volume method or to inject the active compound preparation, or the active compound itself, into the soil. The seed of the plants can also be treated.

In the treatment of pans of plants, the active compound concentrations in the use forms can be varied within a substantial range. They are generally between 1 and 0.0001% by weight, preferably between 0.5 and 0.001% by weight.

In the treatment of seed, amounts of active compound of 0.001 to 50 g, preferably 0.01 to 10 g, are generally required per kilogram of seed.

In the soil, active compound of 0.00001 to 0.1% by weight, preferably from 0.0001 to 0.02% by weight, are required at the site of action.

Preparation and use of the substances according to the invention can be seen from the examples which follow.

PREPARATION EXAMPLES

Example 1

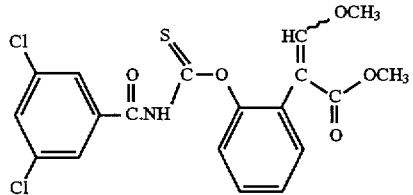

5.9 g (0.025 mol) of 3,5-dichlorobenzoyl isothiocyanate and 2 g (0.02 mol) of triethylamine are added in succession with stirring at 0° C. to a solution of 4.2 g (0.02 mol) of methyl 2-(2-hydroxyphenyl)-3-methoxy-acrylate in 20 ml of absolute tetrahydrofuran. The reaction mixture is subsequently allowed to slowly come to room temperature and is stirred at this temperature for 16 hours. For working up, the solvent is distilled off under reduced pressure, and the residue is purified by chromatography on silica gel (mobile phase: diethyl ether/petroleum ether 1:1).

4.2 g (48% of theory) of methyl 2-[N-(3,5-dichlorobenzoyl)thiocarbamoyloxy)-phenyl]-3-methoxy-acrylate of melting point 131° C. are obtained.

The following 3-methoxy-2-phenyl-acrylic esters of the formula (I) are obtained analogously and following the general preparation instructions:

TABLE 2

| Example Number | R—(O)$_n$— | Physical properties |
|---|---|---|
| 2 | phenyl-O— | $^1$H NMR*): 3.71; 3.84; 7.1–7.5; 7.64 |
| 3 | 4-Cl-phenyl— | m.p. 121° C. |
| 4 | 2-Cl-phenyl— | m.p. 131° C. |
| 5 | 4-H$_3$C-phenyl— | m.p. 110° C. |
| 6 | 4-F-phenyl— | m.p. 110° C. |
| 7 | 3,4-di-Cl-phenyl— | m.p. 109° C. |
| 8 | 3-Cl-phenyl— | m.p. 111° C. |

TABLE 2-continued (Structure I shown at top)

| Example Number | R—(O)ₙ— | Physical properties |
|---|---|---|
| 9 | 2,3-dichlorophenyl | m.p. 216–222° C. |
| 10 | 1-naphthyl | m.p. 119° C. |
| 11 | 2-methylphenyl | m.p. 137° C. |
| 12 | cyclopropyl | ¹H NMR*): 0.8–1.1; 1.3–1.8; 3.59 3.82; 7.0–7.4; 7.63 |
| 13 | CH₃ | ¹H NMR*): 2.14; 3.59; 3.81; 7.0–7.4; 7.62 |

*)The ¹H NMR spectra were recorded in deuterochloroform (CDCl₃) or hexadeuterodimethyl sulphoxide (DMSO-d₆) with tetramethylsilane (TMS) as the internal standard. The data given are the chemical shift as δ value in ppm.

Use Examples

In the use examples which follow, the compound listed below was applied as comparison substance:

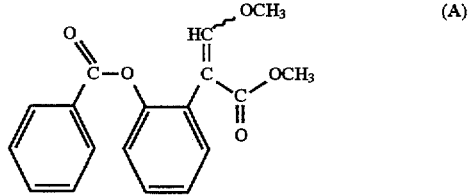

3-Methoxy-2-(2-benzoyloxyphenyl)acrylic ester (disclosed in EP-OS (European Published Specification) 0 178 826)

Example A

Venturia test (apple)/protective

Solvent: 4.7 parts by weight of acetone

Emulsifier: 0.3 part by weight of alkyl-aryl polyglycol ether

To produce a suitable preparation of active compound, one part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous conidia suspension of the apple scab causative organism (Venturia inaequalis) and then remain in an incubation cabin at 20° C. and 100% relative atmospheric humidity for one day.

The plants are then placed in a greenhouse at 20° C. and a relative atmospheric humidity of about 70%.

Evaluation is carried out 12 days after the inoculation.

In this test, a degree of effectiveness of 50% to 100% is shown by the compounds according to the invention disclosed in Examples 1, 2, 3, 4, 5, 6, 7, 8, 10 and 11 at a concentration of 10 ppm in the spray mixture, while the comparison substance (A) shows a degree of effectiveness of less than 30%.

We claim:

1. A 3-methoxy-2-phenyl-acrylic ester of the formula

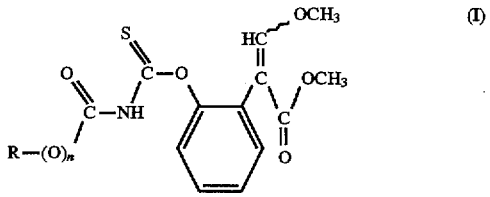

in which

R represents optionally substituted alkyl, optionally substituted cycloalkyl or substituted aryl, and n is 0 or 1 with the exception of methyl 2-[N-(benzoyl)-thiocarbamoyloxy]-phenyl-3-methoxy-acrylate.

2. A 3-methoxy-2-phenyl-acrylic ester according to claim 1, in which

R represents a straight-chain or branched alkyl having 1 to 8 carbon atoms; cycloalkyl having 3 to 8 carbon atoms; $C_6$–$C_{10}$-aryl-$C_1$–$C_6$-alkyl which is optionally monosubstituted to pentasubstituted by identical or different substituents; or $C_6$–$C_{10}$ aryl, monosubstituted to pentasubstituted by identical or different substituents and wherein the substituents on the aryl moieties are halogen, cyano, nitro, formyl, carbamoyl, thiocarbamoyl, straight-chain or branched $C_1$–$C_6$-alkyl, straight-chain or branched $C_1$–$C_6$-alkoxy, straight-chain or branched $C_1$–$C_6$-alkylthio, straight-chain or branched $C_1$–$C_6$-alkylsuphinyl, straight-chain or branched $C_1$–$C_6$-alkylsuphonyl, straight-chain or branched $C_2$–$C_6$-alkenyl, straight-chain or branched $C_2$–$C_6$-alkenyloxy, straight-chain or branched $C_2$–$C_6$-halogenoalkyl, straight-chain or branched $C_1$–$C_6$-halogenoalkoxy, straight-chain or branched $C_1$–$C_6$-halogenoalkylthio, straight-chain or branched $C_1$–$C_6$-halogenoalkylsulphinyl, straight-chain or branched $C_1$–$C_6$-halogenoalkysulphonyl, straight-chain or branched $C_2$–$C_6$-halogenoalkenyl, straight-chain or branched $C_2$–$C_6$-halogenoalkoxy, straight-chain or branched $C_1$–$C_6$-N-alkylamino, straight-chain or branched $C_1$–$C_6$-dialkylamino, straight-chain or branched $C_1$–$C_6$-alkylcarbonyl, straight-chain or branched $C_1$–$C_6$-alkylcarbonyloxy, straight-chain or branched $C_1$–$C_6$-alkoxycarbonyl, straight-chain or branched $C_1$–$C_6$-alkylsulphonyloxy, straight-chain or branched $C_1$–$C_6$-hydroximinoalkyl, straight-chain or branched $C_1$–$C_6$-alkoximinoalkyl, divalent $C_1$–$C_6$-alkylene, divalent $C_1$–$C_6$- dioxyalkylene, each of which is optionally monosubstituted or pentasubstituted by identical or different substituents selected from the group consisting of halogen, straight-chain or branched alkyl having 1 to 4 carbon atoms, straight-chain or branched halogenoalkyl having 1 to 4 carbon atoms and 1 to 9 identical or different halogen atoms, cycloalkyl having 3 to 7 carbon atoms, 3- to 7-membered heterocyclyl having 2 to 6 carbon atoms and 1 to 3 identical or different hetero atoms, phenyl, phenoxy, benzyl, benzyloxy, phenylethyl and phenylethyloxy, each of which is optionally monosubstituted to pentasubstituted in the phenyl moiety by identical or different substituents selected from the group consisting of halogen straight-chain or branched alkyl having 1 to 4 carbon atoms, straight-chain or branched halogenoalkyl having 1 to 4 carbon atoms and 1 to 9 identical or different halogen atoms, straight-chain or branched alkoxy having 1 to 4 carbon atoms and straight-chain or branched halogenoalkoxy having 1 to 4 carbon atoms and 1 to 9 identical or different halogen atoms, n is 0 or 1.

3. A 3-methoxy-2-phenyl-acrylic ester according to claim 1, in which

R represents a straight-chain or branched alkyl having 1 to 6 carbon atoms; cycloalkyl having 3 to 7 carbon atoms; $C_6-C_{10}$-aryl-$C_1-C_4$-alkyl which is optionally monosubstituted to pentasubstituted by identical or different substituents; or $C_6-C_{10}$ aryl, monosubstituted to pentasubstituted by identical or different substituents, and wherein the substituents on the aryl moieties are halogen, cyano, nitro, formyl, carbamoyl, thiocarbamoyl, straight-chain or branched $C_1-C_4$-alkyl, straight-chain or branched $C_1-C_4$-alkoxy, straight-chain or branched $C_1-C_4$-alkylthio, straight-chain or branched $C_1-C_4$-alkylsuphinyl, straight-chain or branched $C_1-C_4$-alkylsuphonyl, straight-chain or branched $C_2-C_4$-alkenyl, straight-chain or branched $C_2-C_4$-alkenyloxy, straight-chain or branched $C_1-C_4$-halogenoalkyl, straight-chain or branched $C_1-C_4$-halogenoalkoxy, straight-chain or branched $C_1-C_4$-halogenoalkylthio, straight-chain or branched $C_1-C_4$-halogenoalkylsulphinyl, straight-chain or branched $C_1-C_4$-halogenoalkysulphonyl, straight-chain or branched $C_2-C_4$-halogenalkenyl, straight-chain or branched $C_2-C_4$-halogenoalkoxy, straight-chain or branched $C_1-C_4$-N-alkylamino, straight-chain or branched $C_1-C_4$-dialkylamino, straight-chain or branched $C_1-C_4$-alkylcarbonyl, straight-chain or branched $C_1-C_4$-alkylcarbonyloxy, straight-chain or branched $C_1-C_4$-alkoxycarbonyl, straight-chain or branched $C_1-C_4$-alkylsulphonyloxy, straight-chain or branched $C_1-C_4$-hydroximinoalkyl, straight-chain or branched $C_1-C_4$-alkoximinoalkyl, divalent $C_1-C_4$-alkylene, divalent $C_1-C_4$-dioxyalkylene, each of which is optionally monosubstituted or pentasubstituted by identical or different substituents selected from the group consisting of halogen, straight-chain or branched alkyl having 1 to 3 carbon atoms, straight-chain or branched halogenoalkyl having 1 to 3 carbon atoms and 1 to 7 identical or different halogen atoms, cycloalkyl having 3 to 6 carbon atoms, 5- to 7-membered heterocyclyl having 4 to 6 carbon atoms and 1 to 2 identical or different hetero atoms, phenyl, phenoxy, benzyl, benzyloxy, phenylethyl and phenylethyloxy, each of which is optionally monosubstituted to trisubstituted in the phenyl moiety by identical or different substituents selected from the group consisting of halogen, straight-chain or branched alkyl having 1 to 3 carbon atoms, straight-chain or branched halogenoalkyl having 1 to 3 carbon atoms and 1 to 7 identical or different halogen atoms, straight-chain or branched alkoxy having 1 to 3 carbon atoms and straight-chain or branched halogenoalkoxy having 1 to 3 carbon atoms and 1 to 7 identical or different halogen atoms, n is 0 or 1.

4. The ester according to claim 1, which has the formula

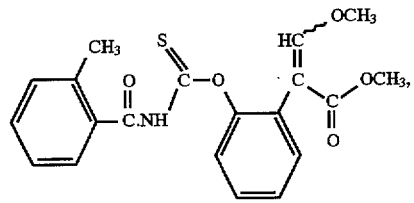

5. A process for preparing a 3-methoxy-2-phenyl-acrylic ester of the formula

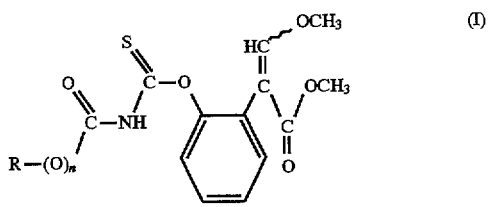

in which

R represents optionally substituted alkyl, optionally substituted cycloalkyl, or substituted aryl, and n is 0 or 1 with the exception of methyl 2-[N-(benzoyl)-thiocarbamoyloxy]-phenyl-3-methoxy-acrylate, which comprises reacting a 2(2-hydroxyphenyl)-3-methoxy-acrylate of the formula

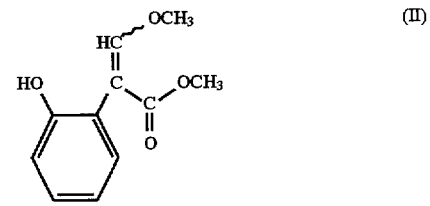

with an N-acyl-isothiocyanate of the formula

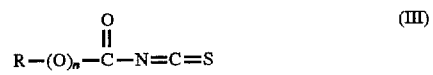

in which

R and n have the abovementioned meaning, optionally in the presence of a diluent and optionally in the presence of an acid-binding agent.

6. A pesticidal composition which comprises a 3-methoxy-2-phenyl-acrylic ester according to claim 1 and an inert carrier.

7. A process for preparing a pesticidal composition which comprises mixing a 3-methoxy-2-phenyl-acrylic ester according to claim 1 with an extender and/or a surface-active substance.

8. A method of combatting pests which comprises applying an effective amount of a 3-methoxy-2-phenyl-acrylic ester according to claim 1 to the pests and/or their environment.

* * * * *